(12) United States Patent
Portune

(10) Patent No.: US 7,314,767 B2
(45) Date of Patent: Jan. 1, 2008

(54) METHOD FOR LOCAL WAFER THINNING AND REINFORCEMENT

(75) Inventor: Richard A. Portune, Sunnyvale, CA (US)

(73) Assignee: Credence Systems Corporation, Milpitas, CA (US)

( * ) Notice: Subject to any disclaimer, the term of this patent is extended or adjusted under 35 U.S.C. 154(b) by 313 days.

(21) Appl. No.: 11/139,706

(22) Filed: May 27, 2005

(65) Prior Publication Data

US 2006/0267009 A1 Nov. 30, 2006

(51) Int. Cl.
*H01L 21/66* (2006.01)

(52) U.S. Cl. .................... 438/16; 438/977; 257/E21.53

(58) Field of Classification Search ................. 324/752
See application file for complete search history.

(56) References Cited

U.S. PATENT DOCUMENTS

| | | | |
|---|---|---|---|
| 3,524,694 A | 8/1970 | Klein | |
| 3,711,186 A | 1/1973 | O'Connor | |
| 3,912,378 A | 10/1975 | Goto | |
| 4,634,234 A | 1/1987 | Baumann | |
| 5,004,307 A | 4/1991 | Kino et al. | |
| 5,208,648 A | 5/1993 | Batchelder | |
| 5,220,403 A | 6/1993 | Batchelder | |
| 5,282,088 A | 1/1994 | Davidson | |
| 5,475,316 A | 12/1995 | Hurley et al. | |
| 5,940,545 A | 8/1999 | Kash et al. | |
| 6,252,412 B1 | 6/2001 | Talbot et al. | |
| 6,462,814 B1 | 10/2002 | Lo | |
| 6,509,750 B1 | 1/2003 | Talbot et al. | |
| 6,591,121 B1 | 7/2003 | Madarasz et al. | |
| 6,594,086 B1 | 7/2003 | Pakdaman | |
| 6,621,275 B2 | 9/2003 | Cotton et al. | |
| 6,720,588 B2 | 4/2004 | Vickers | |
| 6,778,327 B2 | 8/2004 | Pakdaman | |
| 6,921,719 B2 * | 7/2005 | Paterson et al. ............ 438/704 |

OTHER PUBLICATIONS

Dynamics of Backside Wafer Level Microprobing, Chin-Lang Chiang and Daniel T. Hurley, International Reliability Physics Symposium, IEEE, 1998.

* cited by examiner

*Primary Examiner*—Stephen W. Smoot
(74) *Attorney, Agent, or Firm*—Sughrue Mion PLLC; Joseph Bach

(57) ABSTRACT

A method is provided for preparing a semiconductor wafer for testing. The method includes selecting a die to be tested; measuring a diagonal of the die; thinning an area over the die extending beyond the scribe lines, the thinned area may be a circular area having a diameter that is larger than the measured diagonal; providing an insert inside the thinned area; and providing an adhesive on the peripheral area of the insert so as not to obscure the optical path to the die. The insert is advantageously made of an undoped silicon.

12 Claims, 5 Drawing Sheets

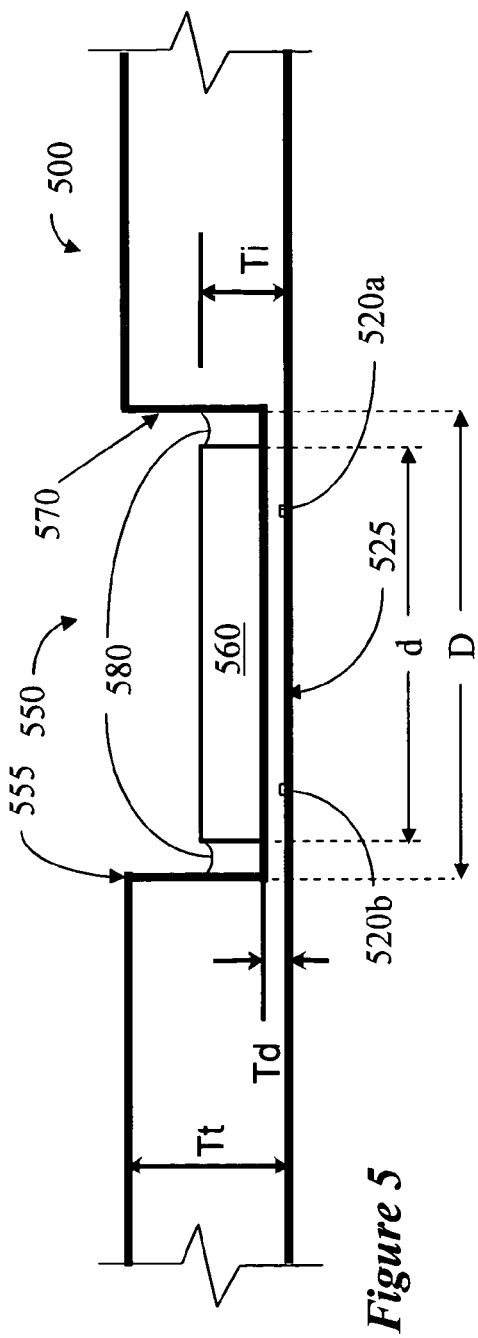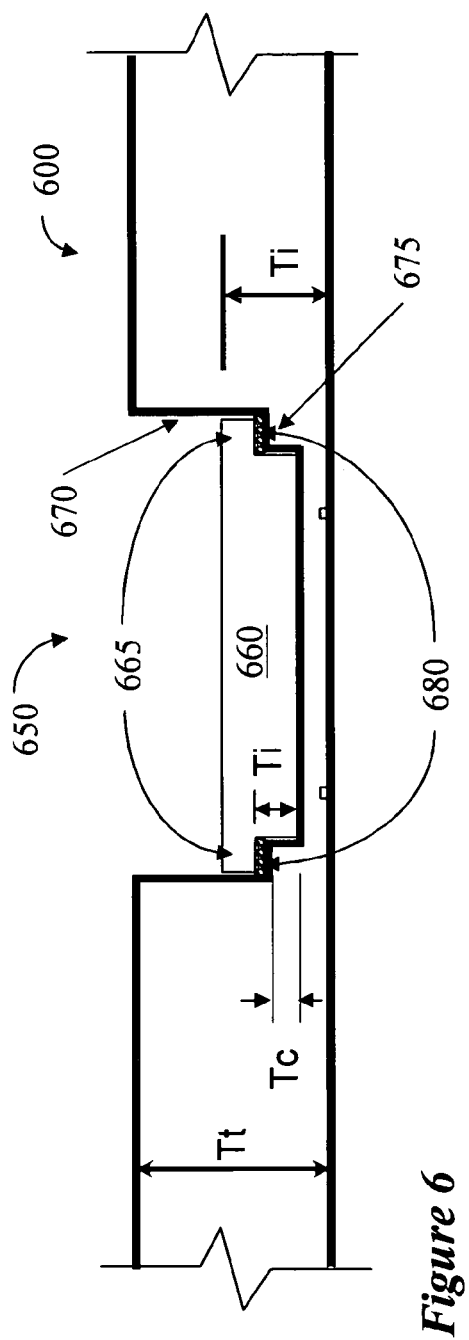
*Figure 5*
*Figure 6*

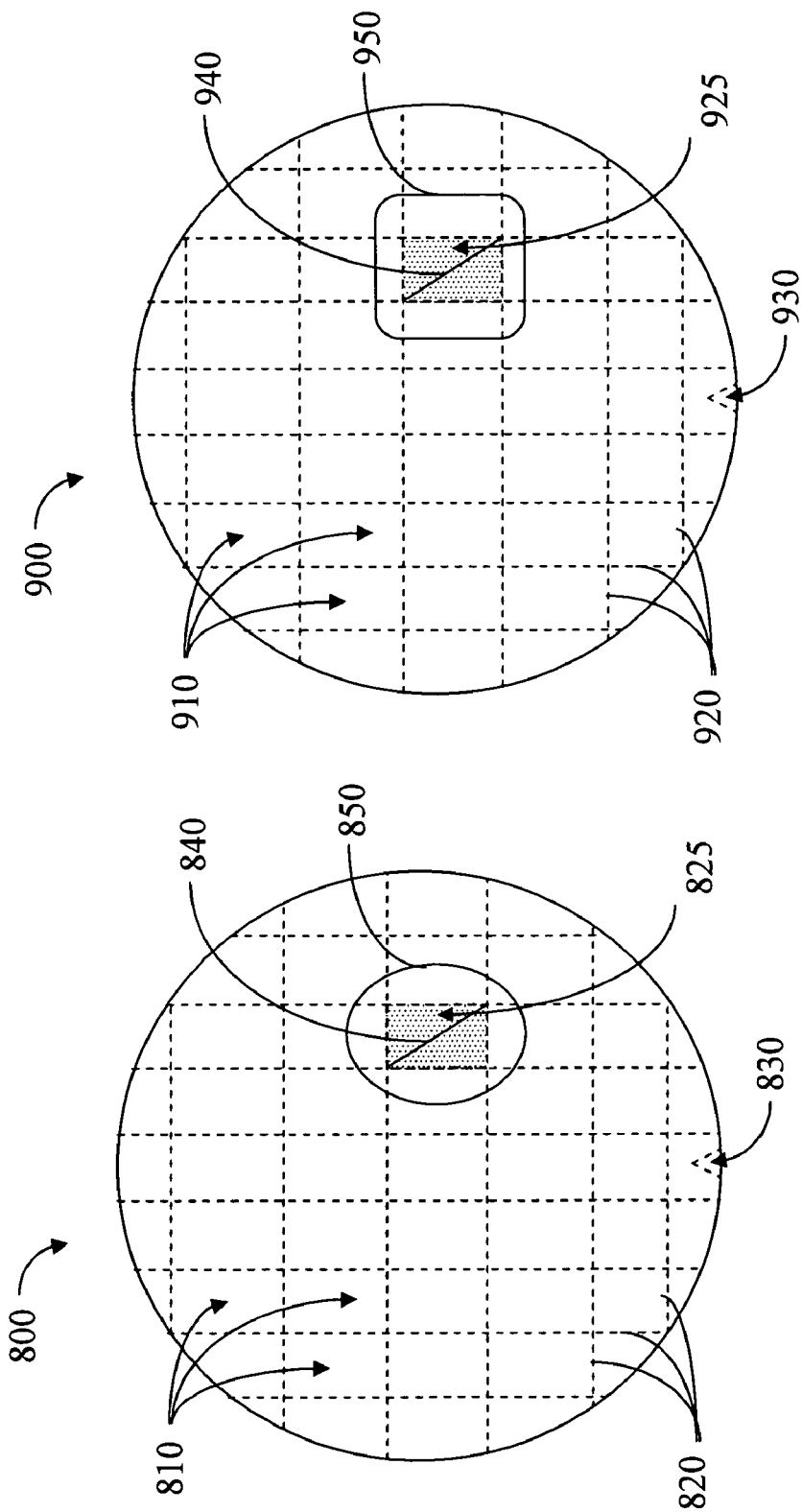

METHOD FOR LOCAL WAFER THINNING AND REINFORCEMENT

BACKGROUND

1. Field of the Invention

The present invention relates to a method for local wafer thinning and reinforcement of the thinned area, and to wafers so fabricated.

2. Description of the Related Art

In the art of integrated circuits (IC's) and wafer testing it is known to use various optical microscopes to illuminate the device under test (DUT) and/or detect optical reflection or emission from the DUT. Modern testing procedures perform the testing from the backside of the DUT, which is mostly silicon having thickness of several hundreds of microns, depending on the particular DUT. Since doped silicon generally absorbs photon illumination, it is very difficult to image the DUT through a thick doped silicon layer. Therefore, it was suggested to thin the wafer down to about 100 microns for observation. On the other hand, thinning the entire wafer to 100 micron would drastically reduce its physical integrity and will probably cause breakage. Therefore, it was previously suggested to thin only the area of interest and keep the rest of the wafer at its original thickness.

FIG. 1 depicts a conventional semiconductor wafer 100 from what is generally referred to as the front side, i.e., the side upon which IC fabrication takes place. For orientation purposes, a notch 130 is provided at the bottom of the wafer. As is known, the wafer is conventionally processed to form multiple IC's, generally referred to as dies, 110, which are separated by scribe lines 120. Once processing of the wafer is completed, the scribe lines are used to separate the dies so as to provide separate IC's. The individual IC's are then encapsulated and are provided with contacts to enable communication with the circuit in which the IC is used. In FIG. 1, die 125 is shaded to indicate that die 125 is the one selected for test.

As can be appreciated, locally thinning the area of die 125 can significantly weaken wafer 100 and can lead to breakage. Notably, applying even a small pressure on die 125 can cause the wafer to break along scribe lines 120. However, many testing procedures include contacting the die 125 with a probe, which exerts pressure on the die. In the prior art it has been suggested to locally thin the wafer and then glue a glass insert inside the thinned area, so as to prevent breakage of the wafer during testing. However, the index of refraction of glass is about 1.4-1.6, while the index of refraction of silicon is about 3.6. Consequently, using such an insert causes optical aberration. Moreover, the adhesive used to glue the insert may introduce additional aberrations—depending on its index of refraction. While the adhesive may be selected so its index of refraction matches that of the glass insert, the combination would still introduce aberrations since the glass insert and adhesive will not match to the doped silicon of the DUT. Accordingly, an improved method for thinning the area of a die, while maintaining the integrity of the wafer is needed.

SUMMARY

Various embodiments of the present invention provide a method for locally thinning a semiconductor wafer, while maintaining the integrity of the wafer.

In one aspect of the invention, a die to be inspected is selected and its diagonal is measured. Then, a circular area having a diameter larger than the measured diagonal is thinned. A transparent insert having a diameter similar to that of the thinned area is prepared placed inside the thinned area so as to physically contact the thinned silicon. An adhesive is then provided only at the perimeter of the insert. According to other embodiments of the invention, the thinned area may not be circular, but it extends beyond the scribe lines of the die to be tested.

According to one aspect of the invention, the insert is made of the same material as the semiconductor wafer. In a specific implementation, the insert is made of polished, undoped silicon, which exhibits superior optical transmission as compared to an unthinned wafer. According to a specific aspect of the invention, the insert is made of an undoped silicon and a solid immersion lens made of silicon is used to optically couple the microscope to the insert, thereby maintaining the index of refraction throughout the entire optical path.

According to an illustrative method of the invention for preparing a semiconductor wafer for testing, the method proceeds using the steps of: selecting a die to be tested; measuring the length of a large diagonal of said die; thinning a circular area over said die, the circular area having a diameter larger than said large diagonal; mounting an insert in said circular area; and, applying an adhesive in a peripheral area of the insert so as not to obscure the optical path to the die. In one specific aspecxt of the invention the circular area comprises a slanted wall. According to another aspect the circular area comprises a vertical wall, and the diameter of the insert is smaller than the diameter of the circular area. According to yet another aspect, the circular area comprises a wall having a wall chamfer provided therein, and the insert comprises a mating chamfer having a thickness larger than thickness of the wall chamfer. In any of the embodiments of the invention, the insert may beneficially and advantageously be made of undoped silicon.

According to another aspect of the invention, a semiconductor wafer that is pre-prepared for optical testing is provided, the wafer comprising: a wafer substrate having a thickness T and a plurality of dies fabricated thereupon, each die having a boundary delineated by scribe lines; at least one thinned area over one of said dies, said thinned area having a boundary extending beyond the scribe lines of said die, said circular area reducing the thickness of said wafer substrate to a thickness t small than thickness T; an insert provided inside said thinned area; and, an adhesive provided on the periphery of said insert so as not to obscure the optical path to the die. In one aspect the area comprises a slanted wall. In another aspect the area comprises a circular area having a vertical wall, and wherein the diameter of said insert is smaller than the diameter of the circular area. According to yet another aspect, the area comprises a wall having a wall chamfer provided therein, and wherein said insert comprises a mating chamfer having a thickness larger than thickness of the wall chamfer. In any of the aspect described, the insert may beneficially and advantageously comprise silicon.

According to yet another aspect of the invention, a method for preparing a semiconductor wafer for testing is provided, the method comprising: selecting a die to be tested, said die being delineated by scribe lines; thinning an area over said die, the area extending beyond the scribe lines; mounting an insert in said area; applying an adhesive in a peripheral area of the insert so as not to obscure the optical path to the die; and placing a solid immersion lens in physical contact with said insert. According to an aspect of the invention the insert is made of an undoped silicon.

According to yet another aspect, the solid immersion lens is made of an undoped silicon. According to a specific aspect of the invention the method further comprises the step of measuring the length of a large diagonal of said die; and wherein the step of thinning an area comprises thinning a circular area having a diameter larger than said large diagonal.

An advantage of the inventive method is that it help maintain the physical integrity of the thinned wafer. Another advantage of the inventive method is that it maintains the index of refraction the same throughout the optical path.

Other aspects and features of the invention will become apparent from the description of various embodiments described herein, and which come within the scope and spirit of the invention as claimed in the appended claims.

BRIEF DESCRIPTION OF THE DRAWINGS

FIG. 5 is a cross-section showing another embodiment of the invention.

FIG. 6 is a cross-section showing yet another embodiment of the invention.

FIG. 8 is a top view showing another embodiment of the invention.

FIG. 9 is a top view showing yet another embodiment of the invention.

Figure 2:
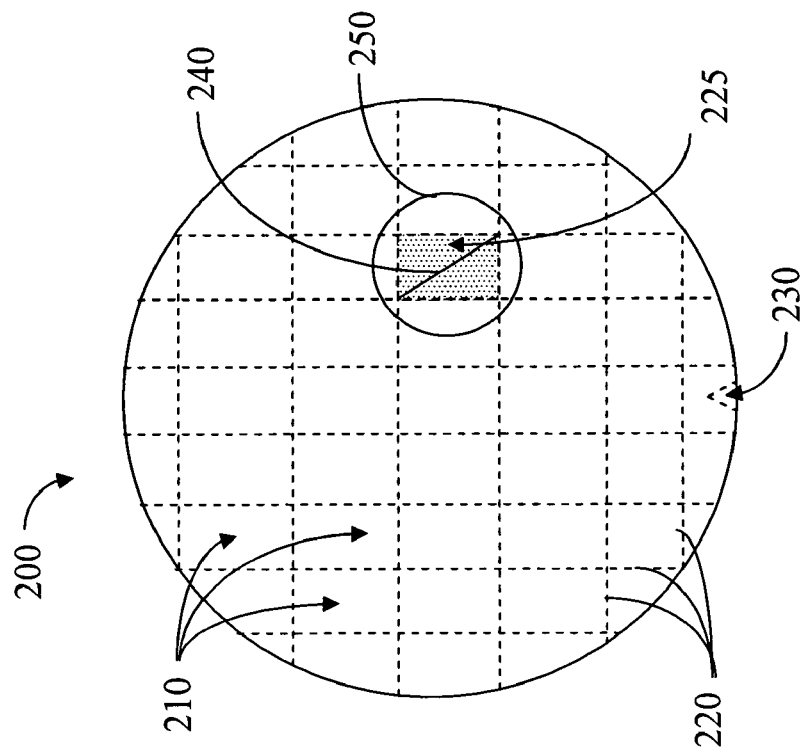
FIG. 2 is a diagram illustrating selection of the area to be thinned from the backside.
Figure 1:
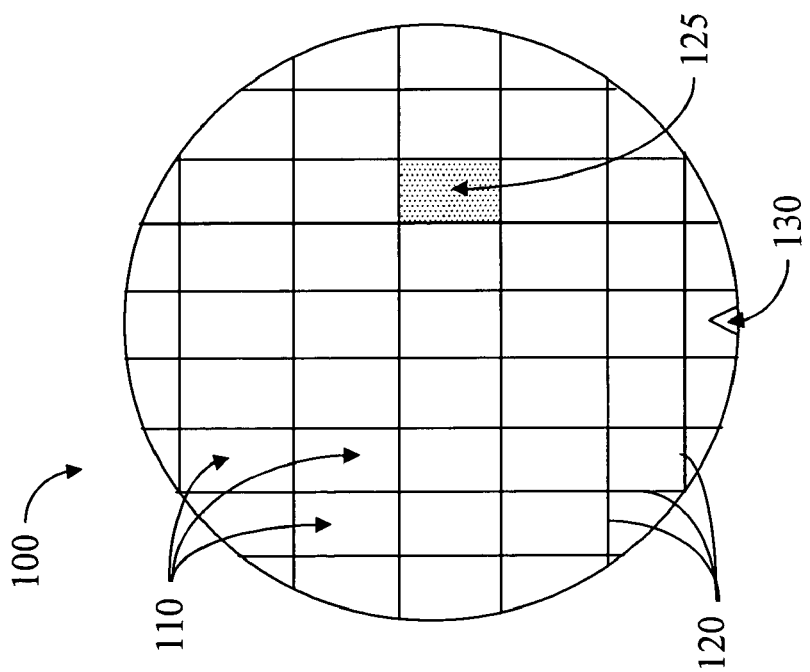
FIG. 1 is a general schematic depicting a semiconductor wafer according to the prior art.

The invention is described herein with reference to particular embodiments thereof, which are exemplified in the drawings. It should be understood, however, that the various embodiments depicted in the drawings are only exemplary and may not limit the invention as defined in the appended claims.

DETAILED DESCRIPTION

An embodiment of the invention will now be described in details with reference to FIGS. 2 and 3. In FIG. 2, wafer 200 is shown from the backside thereof, as indicated by scribe lines 220 being drawn in broken line format. The die 225, that is selected to be inspected, is again shown shaded. As is known, dies 225 would normally be a square or a rectangle having a long diagonal 240. Upon selection of the die to be inspected, its long diagonal 240 is measured. Then, a circular area to be thinned is determined, having a diameter which is larger than the measured diagonal.

Figure 3:
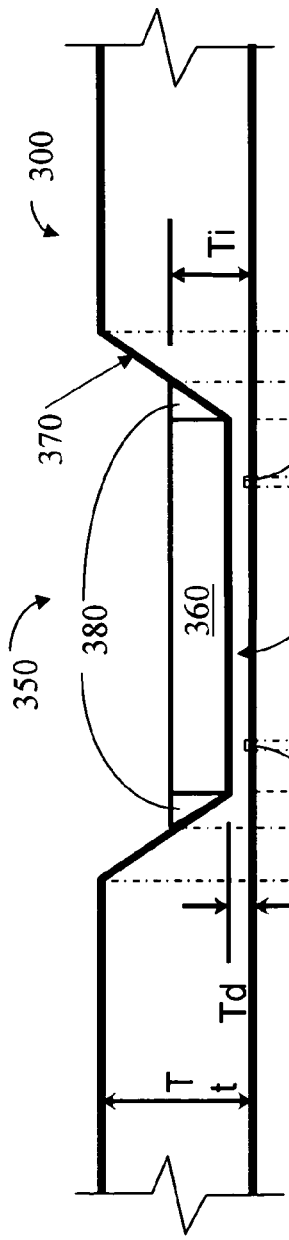
FIG. 3 is a cross section depicting one embodiment of the inventive method.

FIG. 3 is a partial cross-section of a wafer 300 prepared according to one embodiment of the invention. In FIG. 3, the boundaries of die 325 are marked by scribe lines 320a and 320b. The total thickness, Tt, of the wafer is on the order of several hundreds of microns, e.g., 650 microns. An area 350 over die 325 is thinned to a thickness Td of about 100 microns. As is shown, the area 350 has a diameter, D, which makes the thinned area extend beyond scribe lines 320a and 320b. Once the circular area 350 is thinned to about 50-150 microns, a thin insert 360 is provided inside the thinned area. The insert 360 is made of optically transparent material at the wavelength of interest. According to one embodiment, the insert is made of an undoped silicon and has a thickness Ti of about 200-300 microns. Having the insert made of an undoped silicon enhances transmission, as unlike doped silicon, the undoped silicon does not absorb the light. Moreover, since the index of refraction of undoped silicon matches that of the doped silicon of die 325, no optical aberrations are introduced.

As shown in FIG. 3, the walls 370 of thinned area 350 are made to slant so that the opening of thinned area 350 is larger than the diameter D. This arrangement enables applying adhesive 380 is the "ring" area created around the insert 360. Such a fabrication is advantageous as the adhesive is not present in the "line of sight" of the optical probe. Consequently, the light is propagated only through the wafer and the silicon insert, which have similar or the same index of refraction. Therefore, the measurement integrity is preserved and is not affected by the index of refraction of the adhesive used.

Figure 4:
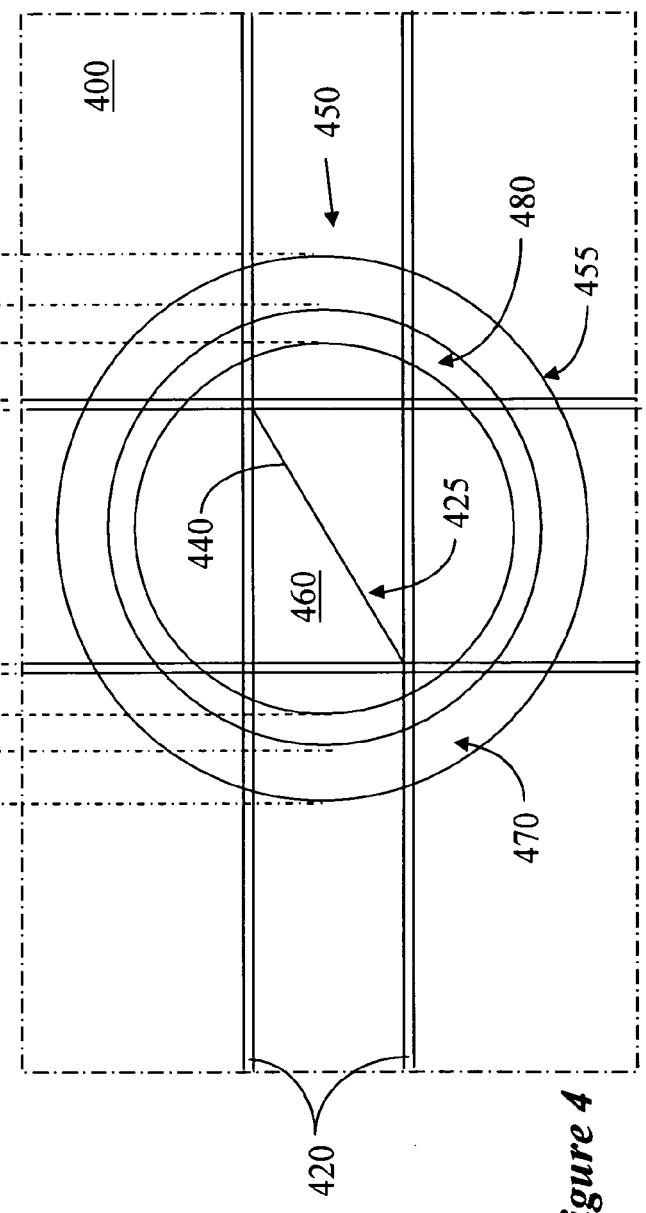
FIG. 4 is a top view of the embodiment shown in FIG. 4.

FIG. 4 is a top view of a part of wafer 400, showing the thinned area 450. Die 425 has the boundaries marked by Manhattan-style scribe lines 420, which define a long diagonal 440. The diameter, D, at the bottom of thinned area 450 is larger than the length of the diagonal 440. The outer rim, 455, of thinned area 450 is larger than the diameter D at the bottom of thinned area 450. This arrangement leaves an area for applying adhesive 480, so as to secure insert 460 inside the thinned area 450. Since the adhesive is provided only at the periphery of the insert, it is outside of the optical path and its index of refraction is irrelevant. Consequently, the adhesive can be chosen according to the requisite properties without regards to its index of refraction property.

FIG. 5 depicts another embodiment of the invention. In FIG. 5, the wall 570 of the thinned area 550 is vertical. Consequently, the diameter at the upper rim 555 of the thinned area is the same as the diameter D. As in the other embodiments, the diameter D is larger than the diagonal of the die 525 to be tested. An insert 560, having a diameter, d, smaller than diameter D, but larger than the diagonal of die 525, is placed centrally in the thinned area, in contact with die 525. An adhesive 580 is then applied to the space between the insert and the walls 570 of the thinned area.

FIG. 6 depicts yet another embodiment of the invention. In FIG. 6 the wall 670 of the thinned area 650 is made so a chamfer or groove 675 is created. A matting chamfer or groove 665 is also fabricated on the insert 660. However, the thickness Ti on the insert is made larger than the thickness Tc on the groove of the thinned area. This ensures that the bottom of the insert 660 comes in physical contact with the thinned area of the wafer 600. Before inserting the insert 660 into the thinned area 650, an adhesive 680 is applied to the groove, as shown by the shaded area.

Figure 7:
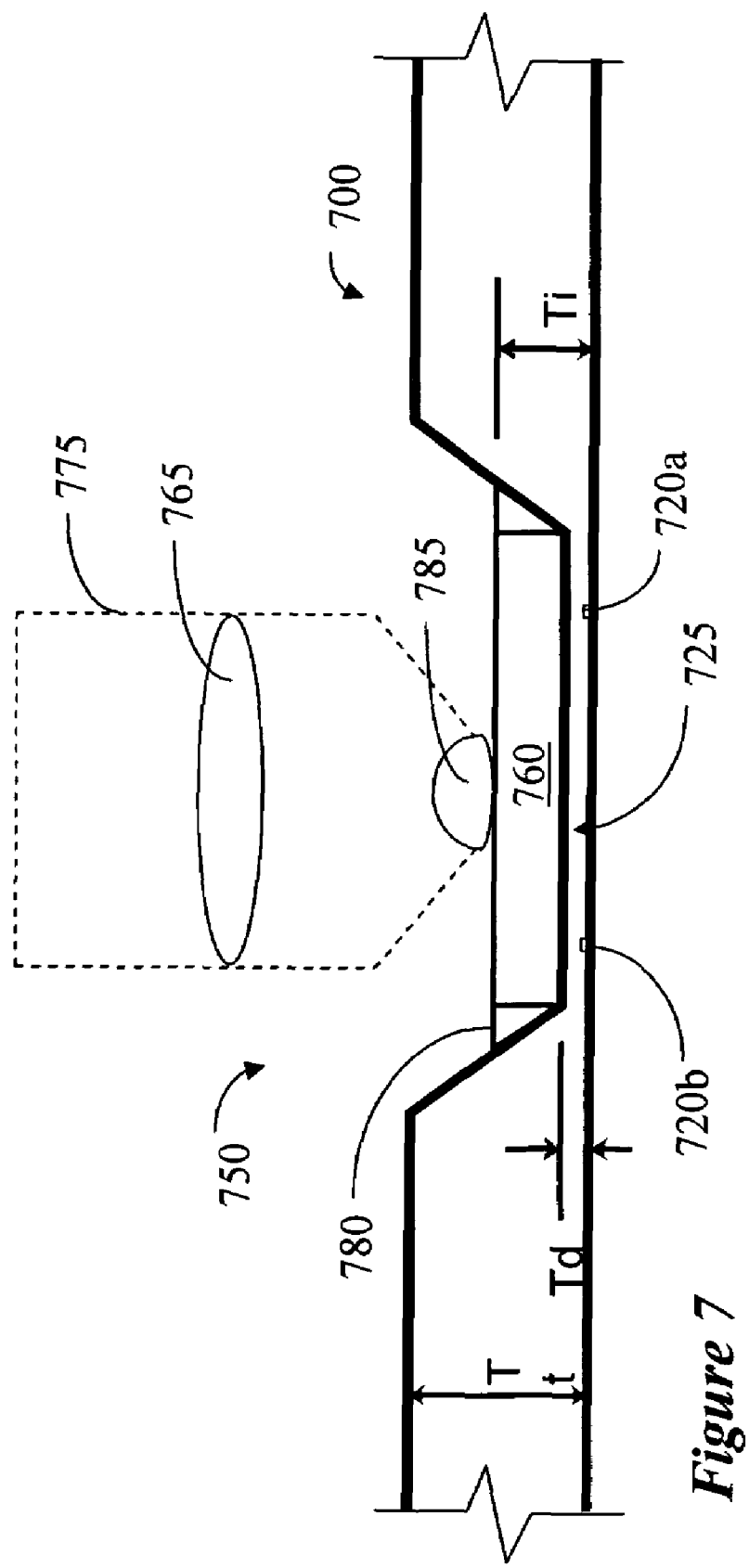
FIG. 7 is a cross-section showing an embodiment of the invention using SIL.

FIG. 7 depicts another embodiment of the invention. In the embodiment of FIG. 7, a solid immersion lens (SIL) 785 is used to optically couple the microscope objective 765 to the DUT 225 (objective housing 775 is shown in broken line as it is of no consequence to the features of the invention). More specifically, in this embodiment the area 750 over the die 725 has been thinned and an insert 760 has been glued at its periphery to the DUT using adhesive 780. In this embodiment, the insert 760 is made of an undoped silicon, so as to provide the advantaged of no light absorption and index matching to the DUT. Similarly, the SIL 785 is also made of undoped silicon. In this manner, light traveling from the DUT, through the insert 760 and the SIL 785 is traveling through matching index of refraction and no optical aberrations are introduced.

In the embodiments described so far, the thinned area and the insert are of circular shape. A circular thinned area is easy to produce and provide the benefit of even distribution of stress, thereby resisting breakage. However, as can be appreciated, other shapes may be produced, so long as they extend beyond the scribe lines. Having the thinned area over, or smaller than, the scribe lines will lead to the prior art failure mode where upon exertion of pressure the die "pops out" of the wafer, as breakage occurs along the scribe lines. FIGS. 8 and 9 depict in top view areas to be thinned, 850, 950, respectively, which are not circular. Area 850 is ellipsoid having its entire boundary extending beyond the scribe lines. Similarly, area 950 is a rounded square having its periphery extending beyond the scribe lines. While a normal square or rectangle may be used, it is believed that a rounded-corner square or rectangle will better resist failure.

While the invention has been described with reference to particular embodiments thereof, it is not limited to those embodiments. Specifically, various variations and modifications may be implemented by those of ordinary skill in the art without departing from the invention's spirit and scope, as defined by the appended claims. Additionally, all of the above-cited prior art references are incorporated herein by reference.

What is claimed is:

1. A method for preparing a semiconductor wafer for testing, comprising:
    selecting a die to be tested;
    measuring the length of a large diagonal of said die;
    thinning a circular area over said die, the circular area having a diameter larger than said large diagonal;
    mounting an insert in said circular area; and,
    applying an adhesive in a peripheral area of the insert so as not to obscure the optical path to the die.
2. The method of claim 1, wherein said insert comprises undoped silicon.
3. The method of claim 1, wherein said circular area comprises a slanted wall.
4. The method of claim 3, wherein said insert comprises undoped silicon.
5. The method of claim 1, wherein said circular area comprises a vertical wall, and wherein the diameter of said insert is smaller than the diameter of the circular area.
6. The method of claim 5, wherein said insert comprises undoped silicon.
7. The method of claim 1, wherein said circular area comprises a wall having a wall chamfer provided therein, and wherein said insert comprises a mating chamfer having a thickness larger than thickness of the wall chamfer.
8. The method of claim 7, wherein said insert comprises undoped silicon.
9. A method for preparing a semiconductor wafer for testing, comprising:
    selecting a die to be tested, said die being delineated by scribe lines;
    thinning an area over said die, the area extending beyond the scribe lines;
    mounting an insert in said area;
    applying an adhesive in a peripheral area of the insert so as not to obscure the optical path to the die; and
    placing a solid immersion lens in physical contact with said insert.
10. The method of claim 9, wherein said insert is made of an undoped silicon.
11. The method of claim 10, wherein said solid immersion lens is made of an undoped silicon.
12. The method of claim 9, further comprising the step of measuring the length of a large diagonal of said die; and wherein the step of thinning an area comprises thinning a circular area having a diameter larger than said large diagonal.

* * * * *